United States Patent [19]

Oeckl et al.

[11] 4,198,428
[45] Apr. 15, 1980

[54] ARYL-THIOCARBOXYLIC ACID THIOCYANOMETHYL ESTERS

[75] Inventors: Siegfried Oeckl, Cologne; Hermann Genth, Krefeld; Wilfried Paulus, Krefeld; Heinz-Joachim Rother, Krefeld; Wilhelm Stendel, Wuppertal; Wilhelm Brandes, Leichlingen; Peter Kraus, Cologne, all of Fed. Rep. of Germany

[73] Assignee: Bayer Aktiengesellschaft, Leverkusen, Fed. Rep. of Germany

[21] Appl. No.: 952,902

[22] Filed: Oct. 19, 1978

[30] Foreign Application Priority Data

Oct. 26, 1977 [DE] Fed. Rep. of Germany ....... 2747825

[51] Int. Cl.² .................. C07C 161/02; A01N 9/18
[52] U.S. Cl. ................................. 424/302; 260/454
[58] Field of Search ................... 260/454; 424/302

[56] References Cited

U.S. PATENT DOCUMENTS 3,095,437   6/1963   Stephens et al. .................. 260/454

*Primary Examiner*—Alan L. Rotman
*Assistant Examiner*—Robert C. Whittenbaugh
*Attorney, Agent, or Firm*—Sprung, Felfe, Horn, Lynch & Kramer

[57] ABSTRACT

An aryl-thiocarboxylic acid thiocyanomethyl ester of the formula

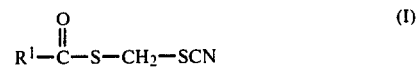

wherein
R¹ represents an optionally substituted aryl radical; a process for preparing the same, a pesticidal composition comprising such aryl-thiocarboxylic acid thiocyanomethyl ester and the use of such aryl-thiocarboxylic acid thiocyanomethyl ester as a pesticide especially for combatting microbes and molluscs. The novel esters are particularly effective agents for protecting industrial materials and living plants.

19 Claims, No Drawings

ARYL-THIOCARBOXYLIC ACID THIOCYANOMETHYL ESTERS

The invention relates to new aryl-thiocarboxylic acid thiocyanomethyl esters, their preparation and their use in pesticides.

New aryl-thiocarboxylic acid thiocyanomethyl esters of the formula

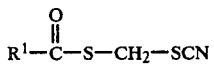
(I)

wherein
R$^1$ represents an optionally substituted aryl radical,
have been found.

Preferred new aryl-thiocarboxylic acid thiocyanomethyl esters are compounds of the formula

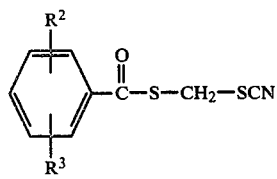
(II)

wherein
R$^2$ and R$^3$ are identical or different and denote hydrogen, halogen, C$_1$ to C$_6$ alkyl, C$_1$ to C$_6$ alkyl which is substituted by halogen, C$_1$ to C$_6$ alkoxy or nitro.

Aryl-thiocarboxylic acid thiocyanomethyl esters of the formula

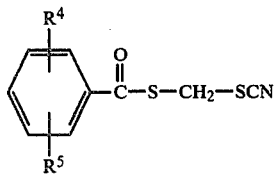
(III)

wherein
R$^4$ and R$^5$ are identical or different and denote hydrogen, chlorine, methyl, ethyl, trifluoromethyl, trichloromethyl, methoxy or ethoxy,
are particularly preferred.

The following aryl-thiocarboxylic acid thiocyanomethyl esters may be mentioned as examples: thiobenzoic acid thiocyanomethyl ester, 4-chloro-thiobenzoic acid thiocyanomethyl ester, 2,5-dichloro-thiobenzoic acid thiocyanomethyl ester, 4-methyl-thiobenzoic acid thiocyanomethyl ester, 2-chloro-thiobenzoic acid thiocyanomethyl ester, 3-methyl-thiobenzoic acid thiocyanomethyl ester, 3-trifluoromethyl-thiobenzoic acid thiocyanomethyl ester and 2,4-dichloro- and 2,4-dibromothiobenzoic acid thiocyanomethyl ester.

Furthermore, a process has been found for the preparation of aryl-thiocarboxylic acid thiocyanomethyl esters, in which aryl-thiocarboxylic acids of the formula

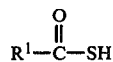
(IV)

wherein
R$^1$ has the abovementioned meaning, are reacted with a compound of the formula $$X-CH_2-R^6 \quad (V)$$

wherein
X denotes halogen and
R$^6$ denotes halogen or the thiocyano group,
in the presence of an acid-binding agent and optionally in the presence of a solvent, and then, if appropriate, the products are reacted with a thiocyanate.

Aromatic optionally substituted hydrocarbon radicals may be mentioned as aryl radicals (R$^1$); the aromatic hydrocarbon radicals can contain, for example, 6 to 18 carbon atoms in the ring system and can be substituted by halogens, nitro groups, alkyl radicals, halogenoalkyl and alkoxy radicals. The following aryl radicals may be mentioned as examples: phenyl, naphthyl, anthracyl and diphenyl.

Halogens (R$^2$, R$^3$, R$^6$ and X) can be fluorine, chlorine, bromine and iodine, preferably chlorine.

Alkyl (R$^2$ and R$^3$) can be a straight-chain or branched hydrocarbon radical with 1 to 6 carbon atoms; examples which may be mentioned are methyl, ethyl, propyl, isopropyl, butyl, isobutyl, pentyl, isopentyl, hexyl and isohexyl, preferably methyl and ethyl.

Halogenoalkyl (R$^2$ and R$^3$) can be a straight-chain or branched hydrocarbon radical with 1 to 6 carbon atoms, which is substituted by fluorine, chlorine, bromine and iodine, preferably fluorine and chlorine; an example which may be mentioned is: trifluoromethyl, trichloromethyl, tribromomethyl, pentachloroethyl, 1,1,1-trichloroethyl and 1,1-dichloro-1-fluoroethyl.

Alkoxy (R$^2$ and R$^3$) can contain a straight-chain or branched aliphatic hydrocarbon radical with 1 to 6 carbon atoms; examples which may be mentioned are methoxy, ethoxy, propoxy, isopropoxy, butoxy, isobutoxy, pentoxy, isopentoxy, hexoxy and isohexoxy.

Preferred arylthiocarboxylic acids for the process according to the invention are compounds of the formula

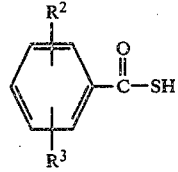
(VI)

wherein
R$^2$ and R$^3$ have the abovementioned meaning.

Arylthiocarboxylic acids of the formula

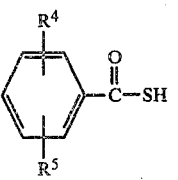
(VII)

wherein
R$^4$ and R$^5$ have the abovementioned meaning,
are particularly preferred for the process according to the invention.

Arylthiocarboxylic acids are known (Beilstein volume 9, 419 I, 169; and Org. Synth. 37, 101) and can be prepared, for example, by reacting an optionally substituted benzoyl chloride with sodium bisulphide.

The following arylthiocarboxylic acids may be mentioned as examples: thiobenzoic acid, 4-chloro-thiobenzoic acid, 2,5-dichloro-thiobenzoic acid, 4-methyl-thiobenzoic acid, 2-chloro-thiobenzoic acid, 3-ethyl-thiobenzoic acid, 3-trifluoromethyl-thiobenzoic acid, 2,4-dichloro- and 2,4-dibromo-thiobenzoic acid.

Possible acid-binding agents for the process according to the invention are organic or inorganic basic compounds, such as tertiary amines, metal alcoholates, metal salts of carboxylic acids, metal carbonates and hydroxides. Metals which may be mentioned are the alkali metals and alkaline earth metals, but also ammonium. It is also possible to use acid-binder salts of the arylthiocarboxylic acids themselves. Examples which may be mentioned are: the triethylammonium salt of the aryl-thiocarboxylic acid, the dimethyl-benzylammonium salt of the aryl-thiocarboxylic acid, the pyridinium salt of the arylthiocarboxylic acid, the sodium salt of the aryl-thiocarboxylic acid and the potassium salt of the aryl-thiocarboxylic acid. Preferred acid-binding agents are sodium methylate and potassium methylate, sodium hydroxide and potassium hydroxide, sodium carbonate and potassium carbonate, dimethylbenzylamine, triethylamine and pyridine. Preferred acid-binder salts are the sodium, potassium and dimethylbenzylammonium salts of thiobenzoic acid, 4'-chloro-thiobenzoic acid, 2,5-dichloro-thiobenzoic acid, 4-methyl-thiobenzoic acid, 2-chloro-thiobenzoic acid, 3-ethyl-thiobenzoic acid, 3-trifluoromethyl-thiobenzoic acid, 2,4-dichloro- and 2,4-dibromo-thiobenzoic acid.

The process according to the invention can be carried out without a solvent, but preferably in the presence of a solvent. Possible solvents are all the solvents which are inert towards the reactants, such as, for example, alcohols, ethers, hydrocarbons and halogenohydrocarbons, such as ethanol, methanol, dioxane, toluene and chlorobenzene, or a reactant, such as the halogenomethyl thiocyanate. It is also possible to carry out the reaction in the presence of water in a two-phase system.

In a preferred embodiment of the process according to the invention, the arylthiocarboxylic acid can be reacted with a halogenomethyl thiocyanate. The reaction can be illustrated by the following equation:

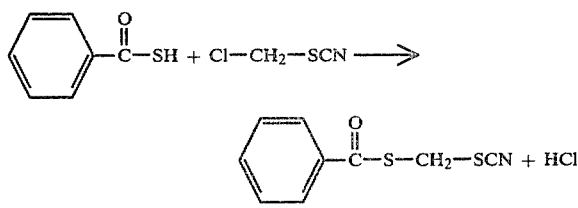

Preferred halogenomethyl thiocyanates within the scope of the formula (V) are compounds of the formula

X—CH$_2$—SCN            (VIII)

wherein
X has the abovementioned meaning.

Chloromethyl thiocyanate is particularly preferred as the halogenomethyl thiocyanate for the process according to the invention.

The preparation of the halogenomethyl thiocyanates is known (Beilstein 3, II, 124) and can be prepared, for example, by reacting dihalogenomethane with one mol of an alkali metal thiocyanate.

In general, the process according to the invention is carried out with equivalent amounts of the reactants. However, it can also be favorable to employ an excess of one or other component. In general, the preferred embodiment of the process according to the invention is carried out in the temperature range from −20° to +100° C., preferably from −10° to +50° C.

After the reaction, the reaction mixture is usually worked up by filtration, evaporation of the solvent and, if appropriate, by washing or recrystallization of the residue.

In another preferred embodiment of the process according to the invention, the preparation of the aryl-thiocarboxylic acid thiocyanomethyl esters according to the invention can be carried out in a first reaction stage by reacting the arylthiocarboxylic acids with a dihalogenomethane to give an arylthiocarboxylic acid halogenomethyl ester, which is reacted with a thiocyanate in a second reaction stage.

The reaction can be illustrated by the following equations:

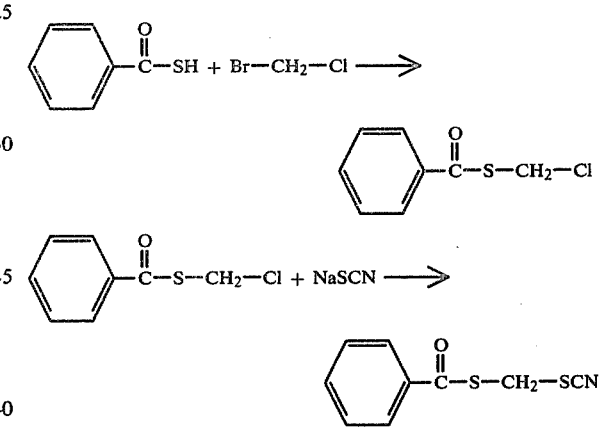

Preferred dihalogenomethanes within the scope of the formula (V) are compounds of the formula

X$^1$—CH$_2$—X$^2$            (IX)

wherein
X$^1$ and X$^2$ are identical or different and represent fluorine, chlorine, bromine or iodine.

Halogenomethanes which contain chlorine and/or bromine are particularly preferred.

The preparation of the dihalogenomethanes is known and can be carried out, for example, by chlorination of methane.

In detail, the following dihalogenomethanes may be mentioned: chloro-bromo-methane, dibromo-methane, chloro-iodomethane and dichloromethane.

The aryl-thiocarboxylic acid halogenomethyl esters of the formula

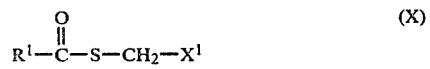

wherein
R$^1$ and X$^1$ have the abovementioned meaning,
formed in the first reaction stage are known (British Pat. No. 1,299,134) and can, of course, be employed for the preparation of the aryl-thiocarboxylic acid thiocyanomethyl esters, the first reaction stage being spared. The following aryl-thiocarboxylic acid halogenomethyl esters may be mentioned as examples: 4-chloro-thiobenzoic acid chloromethyl ester and thiobenzoic acid chloromethyl ester.

Thiocyanates which may be mentioned which are employed for the second reaction stage of the preferred embodiment of the process according to the invention are the alkali metal, alkaline earth metal or ammonium thiocyanates, which can be employed in the molar ratio or also in excess. The following thiocyanates may be mentioned as examples: sodium thiocyanate, potassium thiocyanate and ammonium thiocyanate.

The preferred embodiment of the process according to the invention can be carried out in the temperature range from about 0° to about 150° C., preferably from 50° to 110° C.

It is possible to carry out the first and second reaction stage either in a "one pot process" or a two-stage process, the aryl-thiocarboxylic acid halogenomethyl esters being isolated.

The process according to the invention can be carried out, for example, as follows:

The potassium salt of thiobenzoic acid is stirred in propanol with bromochloromethane at 40° to 60° C. until the reaction has taken place, excess bromochloromethane is distilled off, a slight excess of potassium thiocyanate is added to the reaction mixture and the mixture is heated under reflux for 2 to 3 hours, until the reaction has taken place. For working up, the reaction mixture is concentrated and, after adding water, extracted with organic medium and the end product is isolated by evaporating off the solvent from the organic phase and, if appropriate, is recrystallized or distilled.

In particular, the compounds according to the invention can be used as active compounds for protecting materials, especially industrial materials, against microbial decomposition, for combating molluscs, and in plant protection.

Examples of industrial materials are cooling lubricants, adhesives, coating compositions, resin glues, textile auxiliaries, plastics, leather, dispersions, paints, e.g. opaque paints and other aqueous paints, plasters, and other aqueous solutions or suspensions prone to microbial decomposition. The active compounds according to the invention are particularly suitable for use as preservatives of packaged emulsion paints.

The active compounds according to the invention have a powerful destructive or inhibiting effect on micro-organisms. Examples of micro-organisms which may be mentioned are bacteria, fungi, yeasts, slime organisms, viruses and algae.

Examples of bacteria which may be mentioned are *Escherichia coli, Pseudomonas aeruginosa, Pseudomonas fluorescens, Bacillus subtilis, Bacterium vulgare, Bacillus mycoides* and *Staphylococcus aureus*.

Examples of fungi and yeasts which may be mentioned are *Penicillium glaugum, Rhizopus nigricans, Aspergillus niger, Torula utilis, Candida crusei* and *Candida albicans*.

Examples of algae and slime organisms which may be mentioned are *Phaedodactylum tricornutum Bohlin, Euglena gracilis Klebs, Oscillatoria geminata Meneghini, Stichococcus bacillaris Naegili* and *Aerobacter aerogenes*.

When using the active compounds according to the invention for protecting materials, especially industrial materials, the amount of the active compounds employed depends on the nature and occurrence of the organisms, and on the number of germs in the medium, and can in each case easily be determined by a test series. In general, however, it suffices to employ 0.001% to 0.5% of the active compound, relative to the medium.

The active compounds according to the invention furthermore have an outstanding action against snails, which acts as carriers of human-pathogenic and animal-pathogenic trematodes. Thus, snails are needed as intermediate hosts for the transmission of schistosomes and Fasciola.

For example, *Schistosoma mansoni,* Sambon 1907, is transmitted by *Biomphalaria glabrata* and *Bolinus truncatus*. *Schistosoma haematobium,* Weinland 1858, is transmitted by *Bolinus truncatus* and *Bolinus globosus,* while *Schistosoma japonicum,* Katsurada 1904, is transmitted by Lynmaea spp. and *Fasciola hepatica* is transmitted by Lynmaea spp. Other trematodes transmitted by snails are *Chlohnorchis sinensis, Fasciolopsis buski* and *Paragonimus westermani*.

Since the development of trematodes in the intermediate host is an essential stage in parasites, one can combat, for example, schistosomiasis and pasciolosis, not only in the final host, but also by eliminating the intermediate host and thus interrupting the development cycle of Schistosoma and Fasciola. This prevents the formation of those stages of development of trematodes which can infect man and/or animals.

The agents, according to the invention, for combating snails are employed in the usual manner.

The dosage range to be used in combating snails varies greatly, depending on the species of snails to be combated and on other circumstances.

In general, compounds or solutions which have a concentration of from $10^{-1}$ to $10^{-7}$ parts by weight of active compound are employed. However, higher and lower concentrations are also possible.

A further field of use is the combating of plant diseases in plant protection.

Since the active compounds according to the invention exhibit a powerful fungitoxic and bacteriotoxic action and do not damage crop plants at the concentrations required for combating fungi and bacteria, they are suitable for use as plant protection agents for combating fungal and bacterial diseases.

Fungitoxic agents are employed in plant protection for combating Plasmodiophoromycetes, Oomycetes, Chytridiomycetes, Zygomycetes, Ascomycetes, Basidiomycetes and Deuteromycetes.

Compounds having a bacteriotoxic action are used against phytopathogenic bacteria, for example of the genera Pseudomonas, Xanthomonas, Erwinia and Corynebacterium.

The active compounds according to the invention have a broad spectrum of action and can be used against parasitic fungi and bacteria which attack above-ground plants of plants or attack the plants through the soil, as well as against pathogens which can be transmitted by the seed.

They display a particularly good activity against parasitic fungi on above-ground parts of plants; thus, for example, good effects are achieved against the pathogen of apple scab (*Venturia inaequalis*) and against fungal diseases of cereals, for example the pathogen of cereal rust (*Puccinia recondita*).

As plant protection agents, the active compounds according to the invention can be used for the treatment of seed and for the treatment of above-ground parts of plants.

When they are used as leaf fungicides, the concentrations of active compound in the use forms can be varied within a substantial range. They are, in general, between 0.1 and 0.00001 percent by weight, preferably between 0.05 and 0.0001% based on the total weight of the used form.

The active compounds according to the invention can be converted into the usual formulations, such as solutions, emulsions, suspensions, powders, pastes and granules. These are produced in known manner, for example by mixing the active compounds with extenders, that is to say, liquid solvents, or liquefied gases under pressure, and/or solid carriers, optionally with the use of surface-active agents, that is to say, emulsifying agents and/or dispersing agents and/or foaming agents. In the case of the use of water as an extender, organic solvents can, for example, also be used as auxiliary solvents. As liquid solvents, there are suitable in the main, aromatics, such as xylene, toluene, benzene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such s dimethylformamide and dimethylsulphoxide, as well as water; by liquefied gaseous extenders or carriers are meant liquids which are gaseous at normal temperature and under normal pressure, for example aerosol propellants, such as dichlorodifluoromethane or trichlorofluoromethane; as solid carriers: natural mineral media, such as kaolins, clays, talc, chalk, quartz, attapulgite, montmorillonite or diatomaceous earth, and synthetic mineral media, such as highly-disperse silicic acid, alumina and silicates; as emulsifying agents: non-ionic and anionic emulsifiers, such as polyoxyethylene-fatty acid esters, polyoxyethylene-fatty alcohol ethers, for example alkylaryl polyglycol ethers, alkylsulphonates, alkyl sulphates and arylsulphonates; as dispersing agents: for example sulphite waste liquors and methylcellulose.

The active compounds according to the invention can be present in the formulations and in the mixtures together with other known active compounds, such as fungicides, insecticides, acaricides, namaticides, herbicides, bird repellants, growth factors, plant nutrients and agents for improving soil structure.

The formulations in general contain between 0.1 and 95% by weight of active compound, preferably from 0.5 to 90%.

Surprisingly, the aryl-thiocarboxylic acid thiocyanomethyl esters according to the invention have a higher activity than the known alkyl-thiocarboxylic acid thiocyanomethyl esters (Arch. Pharm. 294, 475 to 478 (1961); Arch. Pharm. 300, 326 to 329 (1967); and Japanese Pat. No. 7,308,492).

In the appropriate use amounts and concentrations, the substances according to the invention also exhibit an acaricidal action and an action against hygiene pests.

The preparation process can be carried out in a simple manner and with high yields.

PREPARATION EXAMPLES

EXAMPLE 1

Thiobenzoic acid thiocyanomethyl ester

A Preparation via thiobenzoic acid chloromethyl ester 35 g (0.35 mol) of triethylamine were added to 49 g (0.35 mol) of thiobenzoic acid at 0°–10° under nitrogen. This mixture was then added dropwise to 91 g (0.7 mol) of bromochloromethane at 0° to 10°, the mixture was then further stirred at room temperature for 16 hours, the solvent was removed on a Rotavapor, the residue was extracted by shaking with ethylene chloride/water and the organic phase was separated off and concentrated. The liquid which remained was distilled in vacuo. 50 g (77%) of thiobenzoic acid chloromethyl ester passed over at 105°–115° under 0.7 to 2 mm Hg.

4.8 g (0.026 mol) of thiobenzoic acid chloromethyl ester and 3.08 g (0.038 mol) of sodium thiocyanate were heated under reflux in 30 ml of n-propanol for 2 hours. The mixture was then concentrated, the residue was extracted by shaking with ethylene chloride/water, the organic phase was separated off and the solvent was distilled off. 5 g of a pale yellowish oil remained, which crystallised after seeding; melting point 45°. (This corresponds to a yield of 93% of the theoretical conversion).

B Preparation using chloromethyl thiocyanate 28 g (0.16 mol) of the potassium salt of thiobenzoic acid were dissolved in 550 ml of methanol, and 17 g (0.16 mol) of chloromethyl thiocyanate were added dropwise at −5°. After slowly warming the reaction mixture to room temperature, it was subsequently stirred at 40° for a further 30 minutes and concentrated, the residue was extracted by shaking with water/ethylene chloride, the organic phase was concentrated and the oily residue was freed from chloromethyl thiocyanate residues by heating to 80°–100°/0.5 to 2 mm Hg for several hours; yield 30 g (this corresponds to a yield of 90% of the theretical conversion).

EXAMPLE 2

4-Chloro-thiobenzoic acid thiocyanomethyl ester 16 g (0.15 mol) of chloromethyl thiocyanate were added dropwise to 31.5 g (0.15 mol) of the K salt of 4-chlorothiobenzoic acid in 200 ml of methanol at 0°–10° and the mixture was then first warmed to room temperature and then to 50°–60°, until the reaction had taken place. The cooled mixture was poured onto 1 liter of cold water, whilst stirring vigorously, and the precipitate was filtered off and dried. Light pink-coloured crystals.

Yield: 31 g (this corresponds to a yield of 85% of the theoretical conversion).

The different solubility of the main product and by-product in methanol and ligroin was utilised for the separation.

40 g of the crude product (2:1) were boiled up in 250 ml of methanol, the insoluble material was filtered off, the filtrate was poured into water and the precipitate was dried: 20 g (ratio 5:1). After recrystallising from 400 ml of ligroin, 15 g of white crystals resulted; melting point 80°.

EXAMPLE 3

2,5-Dichloro-thiobenzoic acid thiocyanomethyl ester

A. Via 2,5-dichloro-thiobenzoic acid chloromethyl ester 214 g (1 mol) of the K salt of 2,5-dichloro-thiobenzoic acid were boiled under reflux in 500 ml of methanol with 259 g (2 mols) of bromochloromethane for 3 hours, the mixture was then concentrated, the residue was extracted by shaking with ethylene chloride/water and the organic phase was concentrated and distilled in vacuo. The fraction obtained at 128°–136° under 1 mm Hg contained the pure chloromethyl ester, which crystallised on cooling. 82 g of slightly yellowish crystals; melting point 76° (this corresponds to a yield of 32% of the theoretical conversion).

56 g (0.22 mol) of the chloromethyl ester and 27 g (0.33 mol) of sodium thiocyanate were heated to the reflux in 150 ml of isobutanol for 2 hours. The mixture was then concentrated, the residue was extracted by shaking with ethylene chloride/water and the organic phase was again concentrated. 53 g of a yello, solidifying oil; after stirring with 70 ml of diethyl ether, white crystals resulted; melting point 86° (this corresponds to a yield of 87% of the theoretical conversion).

B. Preparation with chloromethyl thiocyanate 14.5 g (0.05 mol) of the K salt of 2,5-dichloro-thiobenzoic acid and 6.3 g (0.06 mol) of chloromethyl thiocyanate were reacted and processed as in Example 1 B. 18.5 g of a light brown liquid resulted, which after stirring with ether and standing for 1 day partially crystallised. The solid was separated off: 7.5 g of white crystals; melting point 86° (this corresponds to a yield of 45% of the theoretical conversion).

EXAMPLE 4

4-Methyl-thiobenzoic acid thiocyanomethyl ester 20.5 g (0.11 mol) of the K salt of 4-methyl-thiobenzoic acid and 11.7 g (0.11 mol) of chloromethyl thiocyanate were reacted and processed as in Example 1 B. 22.5 g of a light powder resulted and, after recrystallisation from ligroin, 18 g of white crystals resulted; melting point 55° (this corresponds to a yield of 80% of the theoretical conversion).

EXAMPLE 5

2-Chloro-thiobenzoic acid thiocyanomethyl ester 28.5 g (0.14 mol) of the K salt of 2-chloro-thiobenzoic acid and 15 g (0.14 mol) of chloromethyl thiocyanate were reacted and processed as in Example 1 B. 26.3 g of a yellowish oil having a density of 1.36 (this corresponds to a yield of 77% of the theoretical conversion).

EXAMPLE 6

3-Methyl-thiobenzoic acid thiocyanomethyl ester 10 g (0.052 mol) of the K salt of 3-methyl-thiobenzoic acid and 5.6 g (0.05 mol) of chloromethyl thiocyanate were reacted and processed as in Example 1 B. 9.9 g of an oily liquid having a density of 1.27 (this corresponds to a yield of 79% of the theoretical conversion).

EXAMPLE 7

3-Trifluoromethyl-thiobenzoic acid thiocyanomethyl ester 23 g (0.1 mol) of the K salt of 3-trifluoromethyl thiobenzoic acid and 14.3 g (0.13 mol) of chloromethyl thiocyanate were reacted and processed as in Example 1 B. 19 g of a yellowish oil having a density of 1.4 (this corresponds to a yield of 69% of the theoretical conversion).

EXAMPLE 8

2,4-Dichloro-thiobenzoic acid thiocyanomethyl ester 15.8 g (0.064 mol) of the K salt of 2,4-dichloro-thiobenzoic acid and 6.3 g (0.06 mol) of chloromethyl thiocyanate were reacted and processed as in Example 1 B. 13.5 g of a yellowish oil having a density of 1.45 (this corresponds to a yield of 81% of the theoretical conversion). Use Examples

EXAMPLE 9

The compounds of Table 1, dissolved in a small amount of acetone, are in each case used in concentrations of 0.1 to 100 mg/l in Allens nutrient solution (Arch. Mikrobiol. 17, 34 to 53 (1952)) which contains, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solution is infected with slime organisms (about $10^6$ germs/ml) which have been isolated from the spinning water circuits used in polyamide manufacture. Nutrient solutions which contain the minimum microbistatic concentration (MMC) or higher concentrations of active compound are still completely clear after three weeks' culture at room temperature, that is to say the intense reproduction of the microbes, and formation of slime, observed after 3 to 4 days in nutrient solutions free from active compound, do not occur. The MMC values listed in Table 1 show the antimicrobial activity, against slime organisms, of the active compounds according to the invention (column A).

EXAMPLE 10

A mixed culture of green, blue and brown algae and diatoms (*Stichococcus bacillaris Naegeli, Euglena gracilis Klebs, Chlorella pyrenoidosa Chick, Phormidium foredarum Gromont, Oscillatoria geminata Meneghini* and *Phaedodactylum tricornutum Bohlin*) is introduced into Allen's nutrient solution (Arch. Mikrobiol. 17, 34 to 53, (1952)), which contains 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride per 4 l of sterile water, whilst bubbling air through the solution. After 2 weeks, the nutrient solution has assumed a deep greenblue colour as a result of intensive growth of algae. The destruction of the algae after adding the active compounds according to the invention is recognisable from the decoloration of the nutrient solution. Table 1, column B gives the MMC value for the individual active compounds.

Table 1

Column A: test organisms: slime organisms which are isolated from the spinning water circuits in the manufacture

Table 1-continued

Column B: test organisms: mixed culture of algae; the destructive concentration in mg/l is specified (Example 11)

of polyamide; ... statement of the MMC in mg/l (Example 10)

| Active compound | A | B |
|---|---|---|
| Ar—C(=O)—S—CH$_2$—SCN | | |
| Ar = phenyl | 5–10 | 50–100 |
| = 4-chloro-phenyl | 10–20 | 20–50 |
| = 2,5-dichlorophenyl | 10–20 | 100 |
| = 4-methylphenyl | 5–20 | 20–50 |
| = 2-chlorophenyl | 5–20 | 100 |
| = 3-methylphenyl | 10–20 | 20–50 |
| = 3-trifluoromethylphenyl | 10 | 50–100 |
| = 2,4-dichlorophenyl | 10–50 | 50–100 |

EXAMPLE 11 (ACTION AGAINST MOULD AND YEASTS)

The active compounds shown in Table II are added, to give concentrations of 2 mg/l to 5,000 mg/l, to an agar prepared from beer wort and peptone. When the agar has solidified, it is contaminated with pure cultures of *Penicillium glaucum, Chaetomium globosum* and *Aspergillus niger*. After storage for two weeks at 28° C. and 60 to 70% relative humidity, the MMC is determined. The MMC is the lowest concentration of active compound at which no growth whatsoever of the species of microbe used occurs; it is shown in Table II below.

| Active compound | Penicillium glaucum MMC (mg/l) | Chaetomium globosum MMC (mg/l) | Aspergillus niger MMC (mg/l) |
|---|---|---|---|
| Ar—C(=O)—S—CH$_2$—SCN | | | |
| Ar = phenyl | 5 | 7.5 | 5 |
| = 4-chlorophenyl | 5 | 3.5 | 3.5 |
| = 2,5-dichlorophenyl | 20 | 5 | 3.5 |
| = 4-methylphenyl | 10 | 5 | 7.5 |
| = 2-chlorophenyl | 10 | 2 | 5 |
| = 3-methylphenyl | 10 | 5 | 5 |
| = 3-trifluoromethylphenyl | 20 | 20 | 7.5 |
| = 2,4-dichlorophenyl | 10 | 1.5 | 1 |
| CH$_3$—C(=O)—S—CH$_2$—SCN for comparison | 10 | 20 | 20 |

EXAMPLE 12 (ACTION AGAINST BACTERIA)

An agar which contains bouillon as the nutrient medium is provided with the active compounds, shown in Table III, in concentrations of 1 to 5,000 ppm. The nutrient medium is then respectively innoculated with *Bacterium coli, Bacterium pyocyaneum* or *Aerobacter aerogenes* and the infected medium is kept for 2 weeks at 28° C. and 60 to 70% relative atmospheric humidity. The MMC is the lowest concentration of active compound at which no growth of the species of microbe used takes place.

The MMC values are shown in Table III.

| Active Compound | Bacterium coli MMC (mg/l) | Bacterium pyocyaneum MMC (mg/l) | Aerobacter aerogenes MMC (mg/l) |
|---|---|---|---|
| Ar—C(=O)—S—CH$_2$—SCN | | | |
| Ar = phenyl | 350 | 200 | 50 |
| = 2-chlorophenyl | 200 | 150 | — |
| = 3-trifluoromethylphenyl | 750 | 350 | — |

EXAMPLE 13

Snail test

The test snails used are snails of the species *Biomphalaria glabratus*, which were exposed for 24 hours to an appropriate dilution of the substance to be tested. After a further 24 hours in water free from active compound, the test result is evaluated in comparison to untreated controls.

The result is expressed in %. 100% means that all snails were destroyed and 0% that all snails survived.

Table IV

| Active compound | Active compound concentration in ppm | Destructive action in % against Biophalaria glabrata |
|---|---|---|
| 2-chloro-thiobenzoic acid thiocyanomethyl ester | 10 | 100 |
|  | 3 | 100 |
|  | 1 | <50 |
|  | 0 | 0 |
| 2,5-dichloro-thiobenzoic acid thiocyanomethyl ester | 10 | 100 |
|  | 3 | 0 |
| 3-chloro-thiobenzoic acid thiocyanomethyl ester | 10 | 100 |
|  | 3 | 0 |
| 2,4-dichloro-thiobenzoic acid thiocyanomethyl ester | 1 | 100 |
|  | 0.3 | — |

EXAMPLE 14

The activity of thiobenzoic acid thiocyanomethyl ester against marine algae (*Enteromorpha intestinalis* and Ectocarpus spec.) is determined as follows:

Seawater, prepared from commercially available sea salt, with the additional incorporation of vitamin V 12 (1 mg/l), NaNO$_3$ (100 mg/l), Na$_2$HPO$_4$.12H$_2$O (20 mg/l) and soil decoction (50 ml/l), Biologie der Algen (Biology of the Algae), Georg Thieme Verlag, Stuttgart, 1968) is contaminated with the abovementioned species of algae. After 4 weeks in daylight at 18° C., increasing concentrations (0–100 mg/l) of thiobenzoic acid thiocyanomethyl ester are added to samples of the nutrient solution.

Result:

10–20 mg/l of the substance according to the invention have a destructive effect on *Ectocarpus* spec., and 20–40 mg/l have a destructive effect on *Enteromorpha intestinalis*.

EXAMPLE 15

0–0.5% of thiobenzoic acid thiocyanomethyl ester is added to a commercial emulsion paint. The samples are tested as follows:

A. Preservation of the packaged paint

In the course of 2 months, the paint is contaminated three times with bacteria (*Pseudomonas aeruginosa* and *Escherichia coli*) and moulds (*Aspergillus niger* and *Pullularia pullulans*): about $10^5$ germs/g of emulsion paint.

Result:

In samples which contain 0.1% or more of the substance according to the invention, the microbes introduced are in each case destroyed; these samples exhibit good preservation.

A sample to which the active compound is not added contains more than $10^6$ germs/g at the end of the test period.

B. Mould resistance test on paint films.

Cardboard samples (5×5 cm) are painted on both sides with samples of a commercially available paint and after drying for eight days at room temperature are placed on a glucose nutrient medium in Petri dishes and contaminated with a spore suspension of the following fungi (Report 219 of the Defense Standards Laboratories Maribuyrnong, Australia): *Penicillium citrinum, Stachybotrys atra Corda, Aspergillus flavus Link, Aspergillus ustus, Aspergillus niger, Paecilomyces varioti Bainier, Alternaria tenuis, Cladosphorium herbarum Link et Fries* and *Pullularia pullulans Fusey.*

The contaminated dishes are stored at 28°–30° C. and 90–95% and are tested after 3 weeks.

Result:

Paint films which contain 0.5% or more of the substance according to the invention, relative to the solids content, are free from fungi at the end of the test time and are considered mould-resistant. Paint films free from active compound are completely pervaded by fungus under these conditions.

EXAMPLE 16

Fusicladium test (apple)/(protective)
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid is mixed with the stated amount of solvent, and the concentrate is diluted with the stated amount of water which contains the stated additions.

Young apple seedlings in the 4–6 leaf stage are sprayed with the spray liquid until dripping wet. The plants remain in a greenhouse for 24 hours at 20° C. and at a relative atmospheric humidity of 70%. They are then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants then again come into a greenhouse for 14 days.

15 days after inoculation, the infection of the seedlings is determined. The assessment data are converted to percent infection. 0% means no infection; 100% means that the plants are totally infected.

The active compounds, the concentrations of the active compounds and the results can be seen from the following table V:

Table V

Fusicladium test (apple)/protective

| Active compound | Infection in % at an active compound concentration of 0.0025 |
|---|---|
| C₆H₅—C(O)—S—CH₂—SCN | 40 |
| 4-Cl—C₆H₄—C(O)—S—CH₂—SCN | 0 |
| 2,4-Cl₂—C₆H₃—CO—S—CH₂—SCN | 1 |
| 4-CH₃—C₆H₄—CO—S—CH₂—SCN | 0 |
| 2-Cl—C₆H₄—CO—S—CH₂—SCN | 6 |
| 3-CH₃—C₆H₄—CO—S—CH₂—SCN | 70 |
| 3-CF₃—C₆H₄—CO—S—CH₂—SCN | 26 |
| 2,4-Cl₂—C₆H₃—CO—S—CH₂—SCN | 11 |
| Comparison: H₃C—CO—S—CH₂—SCN | 76 |

EXAMPLE 17

Mycelium growth test
Nutrient medium used:
20 parts by weight of agar-agar
200 parts by weight of potato decoction
5 parts by weight of malt
15 parts by weight of dextrose
5 parts by weight of peptone
2 parts by weight of $Na_2HPO_4$
0.3 part by weight of $Ca(NO_3)_2$
Ratio of solvent mixture to nutrient medium:
2 parts by weight of solvent mixture
100 parts by weight of agar nutrient medium
Composition of the solvent mixture 0.19 part by weight of dimethylformamide
0.01 part by weight of alkylaryl polyglycol ether
1.80 parts by weight of water
2 parts by weight of solvent mixture The amount of active compound required for the desired active compound concentration in the nutrient medium is mixed with the stated amount of solvent mixture. The concentrate is thoroughly mixed, in the stated proportion, with the liquid nutrient medium which has been cooled to 42° C. and is then poured into Petri dishes of 9 cm diameter. Control plates to which the preparation has not been added are also set up.

When the nutrient medium has cooled and solidified, the plates are inoculated with the species of fungi stated in the table and with one bacterium and incubated at about 21° C.

Evaluation is carried out after 4–10 days, dependent upon the speed of growth of the organisms. When evaluation is carried out the radial growth on the treated nutrient media is compared with the growth on the control nutrient medium. In the evaluation of the growth, the following characteristic values are used:
1 no growth
up to 3 very strong inhibition of growth
up to 5 medium inhibition of growth
up to 7 slight inhibition of growth
9 growth equal to that of the untreated control.

The active compounds, the active compound concentrations and the results can be seen from the following table VI:

TABLE VI

Mycelium growth test

| Active Compounds | Active compound concentration (ppm) | Fungi and bacteria | | | | | | | | | | | | | | | |
|---|---|---|---|---|---|---|---|---|---|---|---|---|---|---|---|---|---|
| | | Fusarium Culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicularia sasakii | Xanthomonas oryzae |
| CH$_2$—NH—CS—S—$\diagdown$Zn $\diagup$ CH$_2$—NH—CS—S (comparison) | 10 | 9 | 9 | 9 | 9 | 9 | 5 | 9 | 9 | 9 | 9 | 9 | 5 | 5 | 9 | 9 | 9 |
| O=C—S—CH$_2$—SCN (phenyl) | 10 | 1 | 1 | 1 | 1 | 1 | 1 | 1 | 1 | 1 | 1 | 1 | 1 | 1 | 1 | 1 | 1 |
| O=C—S—CH$_2$—SCN (4-Cl-phenyl) | 10 | 1 | 1 | 1 | 1 | 1 | 1 | 1 | 1 | 1 | 1 | 1 | 1 | 1 | 1 | 1 | 1 |
| O=C—S—CH$_2$—SCN (2,6-diCl-phenyl) | 10 | 1 | 1 | 1 | 1 | 1 | 1 | 1 | 1 | 1 | 1 | 1 | 1 | 1 | 1 | 1 | 1 |
| O=C—S—CH$_2$—SCN (3-CH$_3$-phenyl) | 10 | 1 | 1 | 1 | 1 | 1 | 1 | 1 | 1 | 1 | 1 | 1 | 1 | 1 | 1 | 1 | 1 |
| O=C—S—CH$_2$—SCN (2-Cl-phenyl) | 10 | 1 | 1 | 1 | 1 | 1 | 1 | 1 | 1 | 1 | 1 | 1 | 1 | 1 | 1 | 1 | 1 |
| O=C—S—CH$_2$—SCN (2-Cl,4-CH$_3$-phenyl) | 10 | 1 | 1 | 1 | 1 | 1 | 1 | 1 | 1 | 5 | 1 | 1 | 1 | 1 | 1 | 1 | 1 |
| O=C—S—CH$_2$—SCN (2-Cl,4-CF$_3$-phenyl) | 10 | 1 | 1 | 1 | 1 | 1 | 1 | 1 | 1 | 1 | 1 | 5 | 1 | 1 | 1 | 1 | 1 |
| O=C—S—CH$_2$—SCN (2,3-diCl-phenyl) | 10 | 1 | 1 | 1 | 1 | 1 | 1 | 1 | 1 | 1 | ? | 5 | 1 | 1 | 1 | 1 | 1 |

What is claimed is:

1. Aryl-thiocarboxylic acid thiocyanomethyl ester of the formula

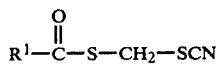

wherein
R¹ represents an aryl radical having 6 to 18 carbon atoms in the ring system which can be substituted by halogens, nitro groups, alkyl radicals, halogeno alkyl and alkoxy radicals wherein said alkyl, halogeno alkyl, and alkoxy radicals contain 1–6 carbon atoms.

2. An aryl-thiocarboxylic acid thiocyanomethyl ester according to claim 1 having the formula

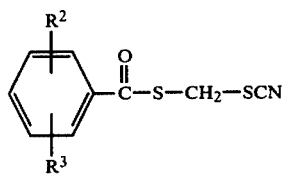

wherein
R² and R³ independently represent hydrogen, halogen, $C_1$ to $C_6$ alkyl, $C_1$ to $C_6$ alkyl which is substituted by halogen, $C_1$ to $C_6$ alkoxy or nitro.

3. An aryl-thiocarboxylic acid thiocyanomethyl ester according to claim 1 having the formula

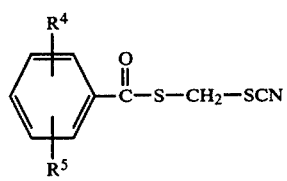

wherein
R⁴ and R⁵ independently denote hydrogen, chlorine, methyl, ethyl, trifluoromethyl, trichloromethyl, methoxy or ethoxy.

4. An aryl-thiocarboxylic acid thiocyanomethyl ester according to claim 1 having the formula

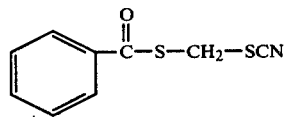

5. An aryl-thiocarboxylic acid thiocyanomethyl ester according to claim 1 having the formula

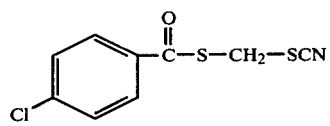

6. An aryl-thiocarboxylic acid thiocyanomethyl ester according to claim 1 having the formula

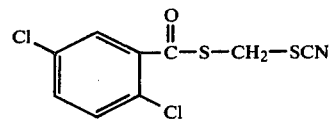

7. An aryl-thiocarboxylic acid thiocyanomethyl ester according to claim 1 having the formula

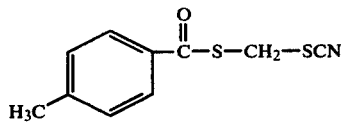

8. An aryl-thiocarboxylic acid thiocyanomethyl ester according to claim 1 having the formula

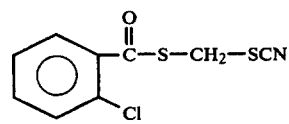

9. An aryl-thiocarboxylic acid thiocyanomethyl ester according to claim 1 having the formula

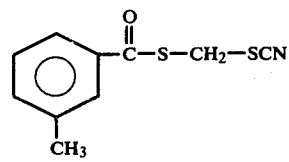

10. An aryl-thiocarboxylic acid thiocyanomethyl ester according to claim 1 having the formula

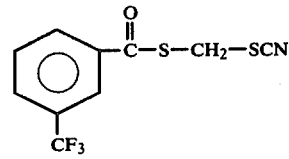

11. An aryl-thiocarboxylic acid thiocyanomethyl ester according to claim 1 having the formula

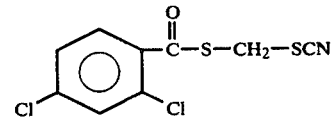

12. A pesticidal composition comprising a pesticidally effective amount of the aryl-thiocarboxylic acid thiocyanomethyl ester according to claim 1 and a carrier.

13. A composition according to claim 12 wherein said aryl-thiocarboxylic acid thiocyanomethyl ester is present in said composition in an amount between 0.1 and 95% by weight.

14. A composition according to claim 13 wherein said aryl-thiocarboxylic acid thiocyanomethyl ester is present in an amount of 0.5 to 90% by weight.

15. A composition according to claim 12 which is in the form of a solution, emulsion, suspension, powder, paste or granule.

16. A process for combatting microbes in a microbial-containing environment which comprises contacting said microbes in said environment with a antimicrobially effective amount of a compound of claim 1.

17. A process according to claim 16 wherein said microbial-containing environment comprises a cooling lubricant, adhesive, coating composition, resin glue, textile auxiliary, plastic, leather, disbursion, paint, plaster or an aqueous solution and said compound is included in the microbial environment in an amount between 0.001 and 0.5% based upon the weight of the microbial-containing environment.

18. A process according to claim 16 wherein said compound is applied to a plant.

19. A process for combatting a mollusc which comprises applying thereto a molluscicidally effective amount of a compound of claim 1.

UNITED STATES PATENT AND TRADEMARK OFFICE
CERTIFICATE OF CORRECTION

PATENT NO. : 4,198,428

DATED : April 15, 1980

INVENTOR(S) : SIEGFRIED OECKL, HERMANN GENTH, WILFRIED PAULUS, HEINZ-JOACHIM ROTHER, WILHELM STENDEL, WILHELM BRANDES and PETER KRAUS It is certified that error appears in the above-identified patent and that said Letters Patent are hereby corrected as shown below:

COLUMN 5, LINE 59: "glaugum" should be --glaucum--.

COLUMN 7, line 51: "namaticides" should be "nematicides"

COLUMN 9, line 25: "yello" should be --yellow--.

COLUMN 10, line 20 "Use Examples" should start a new line.

COLUMN 11, line 35, Insert -- Table II

Record of the MMC in mg/l for the action of the active compounds shown below on moulds and veasts. --

UNITED STATES PATENT AND TRADEMARK OFFICE
CERTIFICATE OF CORRECTION

PATENT NO. : 4,198,428                        Page 2 of 2
DATED : April 15, 1980
INVENTOR(S) : SIEGFRIED OECKL, HERMANN GENTH, WILFRIED PAULUS, HEINZ-JOACHIM ROTHER, WILHELM STENDEL, WILHELM BRANDES and PETER KRAUS.

It is certified that error appears in the above-identified patent and that said Letters Patent are hereby corrected as shown below:

COLUMN 12, LINE 1,    Insert --Table III

Record of the MMC values in mg/1 for the action of the active compounds shown below on bacteria. --

Signed and Sealed this

Twelfth Day of August 1980

[SEAL]

Attest:

SIDNEY A. DIAMOND

Attesting Officer        Commissioner of Patents and Trademarks